United States Patent [19]

Moody

[11] Patent Number: 4,753,115

[45] Date of Patent: Jun. 28, 1988

[54] PULLOUT FORCE MEASURING APPARATUS

[75] Inventor: Albert Moody, Atlanta, Ga.

[73] Assignee: F.C. Brown Company, Atlanta, Ga.

[21] Appl. No.: 933,978

[22] Filed: Nov. 24, 1986

[51] Int. Cl.⁴ .......................... G01L 5/00; G01N 3/08
[52] U.S. Cl. .................................... 73/862.01; 73/826; 73/862.53
[58] Field of Search ........... 73/862.01, 862.53, 862.58, 73/803, 826, 827, 831, 833, 834, 837, 841, 842, 845, 761

[56] References Cited

U.S. PATENT DOCUMENTS

| 3,563,087 | 2/1971 | Brunelle et al. | 73/862.01 X |
| 3,738,163 | 6/1973 | McEntire | 73/862.01 X |
| 4,662,227 | 5/1987 | Peterson | 73/826 X |

FOREIGN PATENT DOCUMENTS

| 2747329 | 4/1979 | Fed. Rep. of Germany | 73/826 |
| 1428981 | 3/1976 | United Kingdom | 73/761 |

*Primary Examiner*—Charles A. Ruehl
*Attorney, Agent, or Firm*—Jones, Askew & Lunsford

[57] ABSTRACT

A device for measuring the amount of tensile force required to remove a roof fastener from a roof supporting structure. The device includes a base, a sliding parallel shaft assembly, a hydraulic cylinder, and a threaded screw. The lower end of the sliding shaft assembly engages the head of the fastener. The threaded screw threadably engages the upper platform of the sliding shaft assembly, and has a lower end biasing upon the piston of the hydraulic cylinder. As the threaded screw tightened downwardly, the lower end of the screw pushes the piston downwardly such that the fluid within the cylinder is compressed. Simultaneously, the sliding shaft assembly is drawn upwardly such that a tensile force is applied to the fastener. A pressure gauge determines the pressure level within the cylinder, which, by calibration of the like, may be used to determine the amount of tensile force exerted upon the fastener. A needle follower may be provided in the pressure gauge to determine the maximum force exerted upon the fastener prior to its removal.

11 Claims, 2 Drawing Sheets

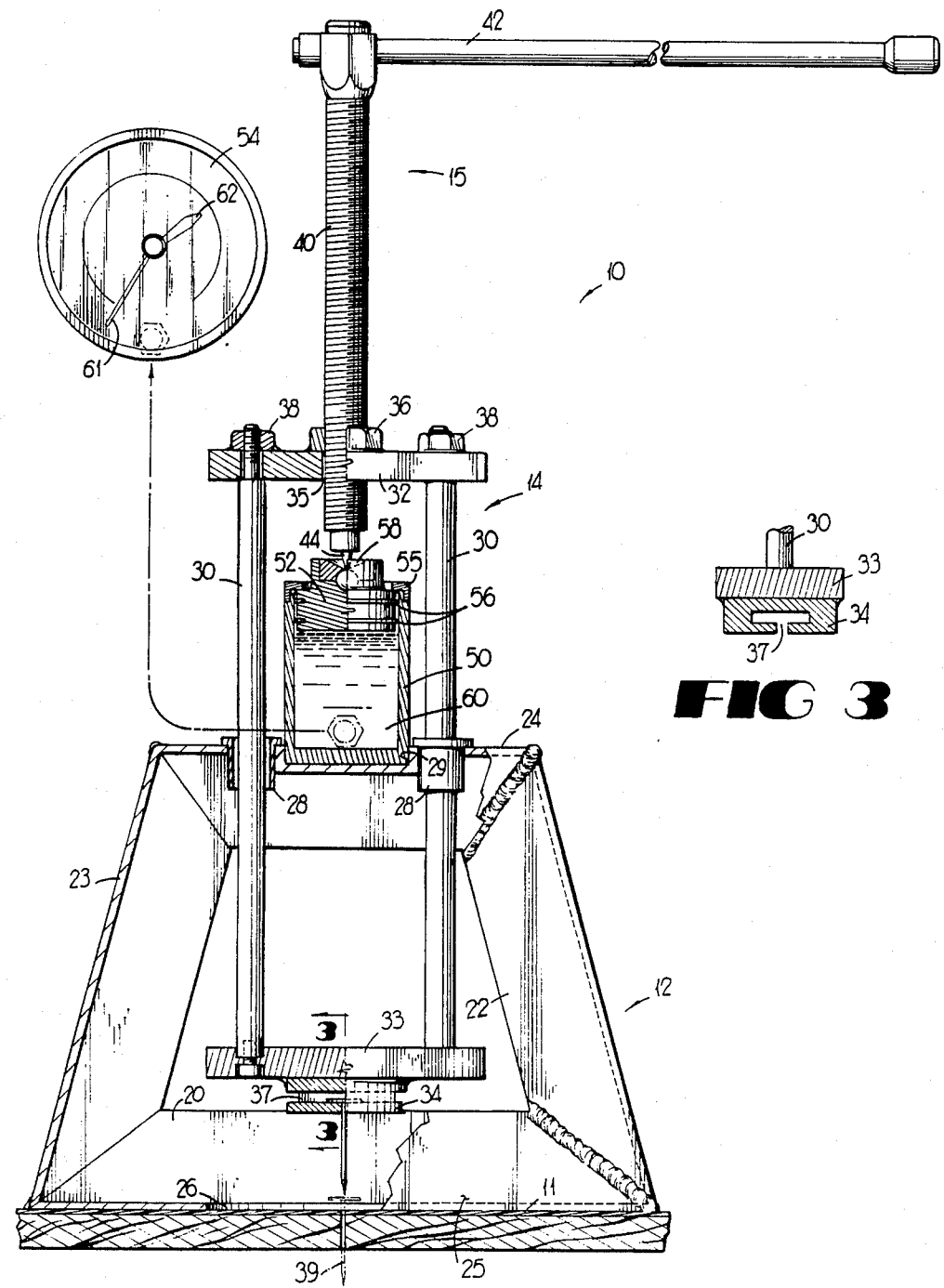

PULLOUT FORCE MEASURING APPARATUS

FIELD OF THE INVENTION

The present invention relates to force measuring devices, and more particularly, to a device which measures the tensile force required to remove a roof fastener from a roof supporting structure.

In roofing construction, it is common to utilize fasteners to secure roofing material atop supporting structures. These fasteners commonly include a head which engages the roofing material, and a shank portion, which passes through the roofing material to engage the underlying supporting structure. As the exterior of the structures may be subjected to various weather conditions, including high winds, it is advantageous to provide an effective engagement between the fasteners and the supporting structure, to prevent inadvertent detachment of the roofing material from the supporting structure. It is also advantageous to have a means for determining the effectiveness of the fastener engagements, in order that a cost-effective, yet sufficient number of fasteners may be provided.

Therefore it has been known to provide various testing devices to determine the effectiveness of the the fastener engagements. Most of these testing devices are directed toward determining the maximum amount of tensile force, or the "pullout" force required to remove a sample of representative fasteners from their installed positions. This determination allows for a reasonable estimate of the effectiveness of the remaining fasteners.

Prior devices known to the applicant have utilized a hydraulically driven fastener pulling head which removes the fasteners from the supporting structure. Measurement of the amount of tensile force required to remove the tested fastener has been determined by monitoring the maximum fluid pressure reached during removal of the fastener, and mathematically calculating the amount of tensile force exerted upon the fastener by the pulling head at the fluid pressure required for pullout.

The prior-art hydraulically driven testing apparatus typically include some type of hydraulic pump, which is relatively heavy and not easily transported to the top of building structures, a separate hydraulically-powered device to engage and extract fasteners, and a length of hose interconnecting the pump and the extracting device. This often results in the apparatus being inadvertently dropped from the ladders or rooftops during transport, creating a risk of equipment damage or human injury. Furthermore, the devices are mechanically complex, difficult to operate, and expensive to purchase and maintain.

Therefore it is desirable to have a lightweight, inexpensive roof fastener testing device which is simple to operate and maintain.

SUMMARY OF THE INVENTION

The present invention solves problems in the prior art by providing a lightweight, inexpensive roof fastener testing device which is simple to operate and maintain. The device in general includes a base for placement upon the supporting member, fastener gripping means operably associated with said base, means for exerting a tensile force on said fastener gripping means relative to said base so as to withdraw the fastener from the supporting member, and force measuring means operably associated with said force exerting means to measure the force required to withdraw the fastener from the supporting member.

Stated somewhat more particularly, the present device includes a base, a sliding parallel shaft assembly, a hydraulic cylinder, and a threaded screw. The base includes a base support and a platform space upwardly from the base support. The hydraulic cylinder includes an upwardly disposed cylinder situated atop the platform, and a piston head which encapsulates fluid within the cylinder. The sliding parallel shaft assembly includes upper and lower plate members, and a pair of parallel shafts having one end attached to each of the plate members. The parallel shafts loosely fit within bushings located within the upper platform of the base. The lower plate of the sliding shaft assembly includes a fastener gripping means for engaging the head of the fastener. The threaded screw threadably engages the upper platform of the sliding shaft assembly, and has a lower end biasing upon the piston of the hydraulic cylinder. As the threaded screw is tightened downwardly, the lower end of the screw pushes the piston downwardly such that the fluid within the cylinder is compressed. Simultaneously, the sliding shaft assembly is drawn upwardly such that a tensile force is applied to the fastener. A pressure gauge determines the pressure level within the cylinder, which, by calibration of the like, may be used to determine the amount of tensile force exerted upon the fastener.

OBJECTS OF THE INVENTION

It is an object of the present invention to provide an improved roof fastener testing device.

It is another object of the present invention to provide an improved roof fastener testing device which is easy to operate and maintain.

It is another object of the present invention to provide an improved roof fastener testing device which is lightweight and easy to manipulate.

It is another object of the present invention to provide an improved roof fastener testing device which is accurate and reliable.

DESCRIPTION OF THE DRAWINGS

FIG. 2 is a partial cutaway front elevation view of the testing device of FIG. 1.

FIG. 3 is an isolated section view taken along line 3—3 of FIG. 2, showing the pulling head used in the disclosed embodiment.

DETAILED DESCRIPTION OF PREFERRED EMBODIMENT

Figure 1:
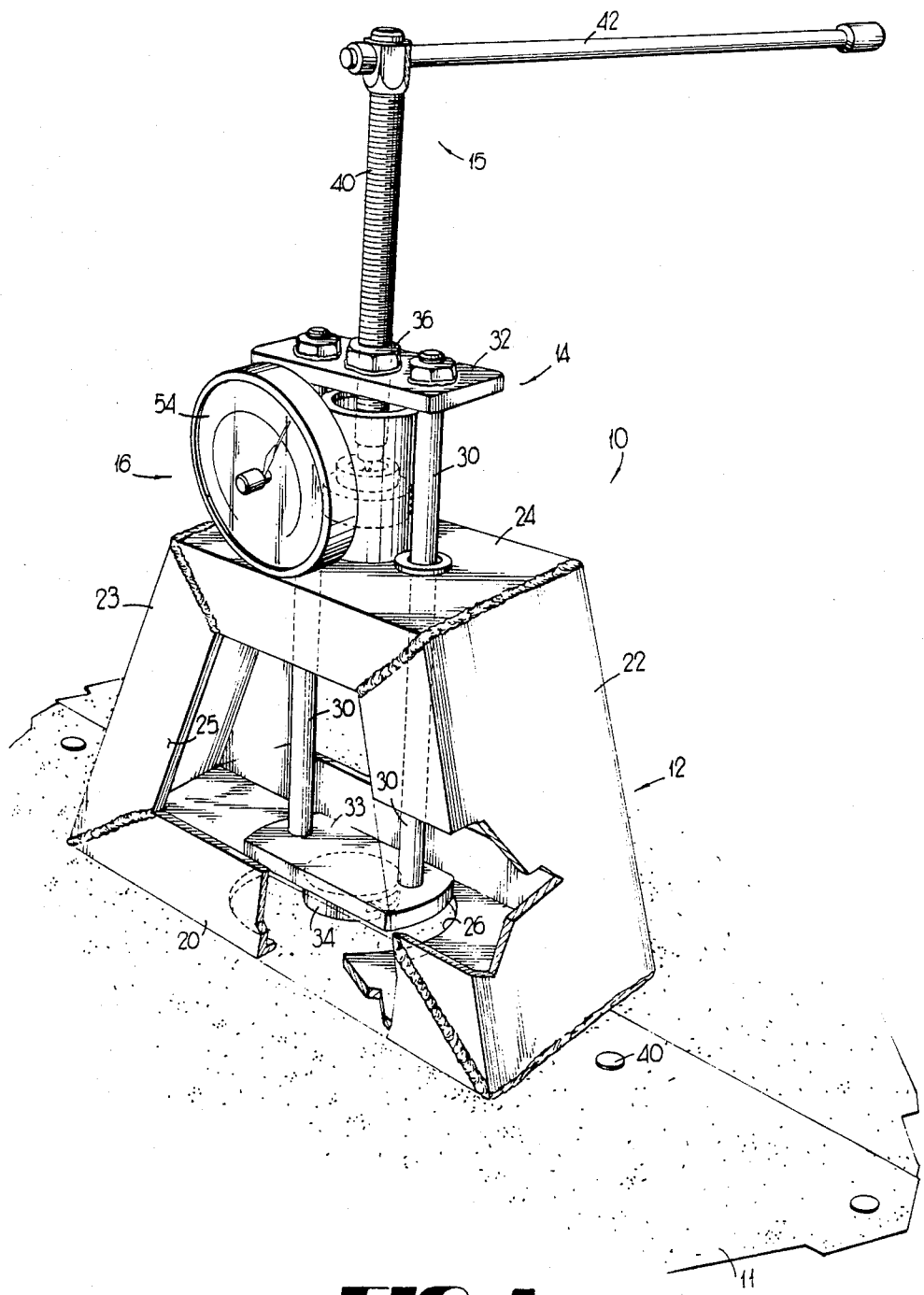
FIG. 1 is a pictorial illustration of the roof fastener testing device in a preferred embodiment of the present invention.

Referring now to the drawings, in which like numerals represent like parts throughout the several views, the pullout force measuring apparatus 10 of the preferred embodiment rests upon a typical roof surface 11 during operation, and includes a base 12, a sliding parallel shaft assembly 14, a screw assembly 15, and a compression force measurement assembly 16.

For purposes of effective explanation, references may be made to "upper", "lower", "right", or "left" portions of various elements throughout this description. It should be understood that such references are merely relative terms, as the preferred embodiment may be used in a variety of positions, and are made only in reference to the views shown in FIGS. 1, 2, and 3. Therefore it should be understood that an "upper" planar face of a particular element is that face shown upwardly disposed in the drawings, although that face need not necessarily be so disposed during operation of the preferred embodiment of the present invention.

Referring now to FIGS. 1 and 2, the base 12 is of a unitary construction and includes a floor plate 20, right and left side legs 22, 23, and a top platform 24. The floor plate 20 is substantially platelike and rectangular, is configured for placement upon a flat surface, and defines a circular hole 26 extending through approximately the center of the floor plate and having a substantially vertical central axis. The right and left side legs 22, 23, extend upwardly from the ends of the floor plate 20 on opposite sides of the circular hole 26, and combine to support the top platform 24 above the floor plate such that the primary planar surfaces of the top platform are parallel to the primary planar surfaces of the floor plate. The top platform 24 supports a pair of slide bushings 28 having parallel vertical longitudinal bores extending through the top platform. The upper surface of the top platform 24 also defines an upwardly disposed circular recess 29, located at approximately the midpoint between the slide bearings 28.

The entire base 12 is preferably fabricated from a sheet-metal stamping, folded to form the floor plate, side legs, and top. Gusset plates 25 extend inwardly from the floor plate and side legs, strengthening the trapezoid-shaped base 12.

The sliding parallel shaft assembly 14 includes two elongate parallel shafts 30 extending through the bushings 28 and having upper and lower ends, an upper end plate 32, a lower end plate 33, and a pulling head 34 on the under side of the lower end plate. The shafts 30 are elongate, each have a similar circular cross section, and are substantially the same length. The upper end plate 32 and the lower end plate 33 are substantially platelike and have a substantially rectangular configuration, except that the minor side edges of the lower end plate are slightly rounded to allow the lower end plate to pass through the circular hole 26 in the floor plate 20, as discussed below in further detail. The upper end plate 32 defines a circular hole 35 passing through approximately the center of the upper end plate, and a fixed hex nut 36 is fastened to the upper end plate, such that the bore axis of the fixed hex nut is substantially colinear to the bore axis of the circular hole 35. The inner diameter of each bushing 28 is substantially greater than the diameter of the shafts 30, permitting substantial angular misalignment of the shafts through the bushings.

Referring also now to FIG. 3, the pulling head 34 is substantially disc-shaped, and includes an inverted channel 37 having a "T"-shaped transverse cross section, which extends across the diameter of the lower circular face of the pulling head. As discussed in detail later herein, the channel 37 is configured to accept the head 40 (FIG. 1) of a typical fastener 39, such that the pullout force measuring apparatus 10 can remove the fastener from a supporting member such as the roof surface 11 by tensile force.

The upper ends of the shafts 30 are threaded, and pass through the upper end plate 32 to accept corresponding hex nuts 38, such that the upper ends of the shafts are fixed to the upper end plate, and such that the longitudinal axes of the parallel shafts 30 are mutually normal to the primary planar surfaces of the upper end plate. The lower ends of the shafts 30 are similarly fixed to the lower end plate 33, such that the primary planar surfaces of the lower end plate 33 are substantially parallel to the primary planar surfaces of the upper end plate 32. The pulling head 34 is attached to the lower side of the lower end plate 33 by welding or other means known in the art, such that the T-shaped channel is disposed downwardly.

The screw assembly 15 includes an elongate threaded member 40 having an upper and a lower end, and an elongate handle member 42. The lower end of the threaded member 40 defines a downwardly disposed spike 44, and the upper end of the threaded member defines a bored hole (not shown) having a bore axis substantially perpendicular to the longitudinal axis of the threaded member 40. The handle member 42 fits within the bored hole in the upper end of the threaded member 40 such that the longitudinal axis of the handle member is substantially perpendicular to the threaded member. The handle member 42 may slide freely relative to the threaded member, or may be rigidly fixed to the threaded member.

The compression force measurement assembly 16 includes an upwardly disposed open-ended cylinder 50 having a circular inner bore, a floating piston 52 received in the bore, a fluid pressure measuring gauge 54 mounted on the cylinder (FIG. 1) in fluid communication with the bore of the cylinder, and a retaining collar 55 closing the open end of the cylinder and retaining the piston 52 therein. The piston 52 has an outer cross section slightly less than the inner bore of the cylinder 50. Sealing rings 56 are provided about the circumferential surface of the piston 52 which allow the piston to slidably fit within the inner bore of the cylinder, while maintaining a fluid-tight seal between the walls of the cylinder and the piston. The upper end of the piston 52 defines a conical depression 58 configured to accept the spike 44 at the end of the threaded member 40, as discussed in further detail later herein. The gauge 54 preferably is mounted directly on the cylinder 50 as shown in FIG. 1, but is depicted in FIG. 2 removed from the cylinder for illustration.

When assembled, the compression force measuring assembly 16 contains a relatively incompressible fluid 60 which is captured inside the cylinder 50 by the piston head 52. A threaded retaining collar 55 threadably accepts the outside rim of the open end of the cylinder 50, and provides an interior annular shoulder about the mouth of the cylinder to retain the piston within the cylinder.

As previously discussed, the sealing rings 56 maintain an effective seal between the piston 52 and the inner walls of the cylinder 50. Therefore it may be seen that if the piston 52 is forced downwardly into the cylinder, the piston encounters resistance from the fluid 60 within the cylinder, and the pressure of the fluid 60 rises in direct proportion with the amount of downward force applied to the piston 52. The pressure of the fluid 60 is measured by the fluid pressure measuring gauge 54. By knowing the cross section of the bore of the cylinder 50, the amount of downward force applied to the piston 52 may be determined by conventional math processes, and a "multiplier" constant may be determined, which may be multiplied to the fluid pressure reading to determine the force on the piston. Preferably, the cross section of the cylinder 50 is one square inch, so that a gauge 50 calibrated in "pounds/in$^2$" can be read directly in pounds of tensile pulling force. For example, if the pressure within the cylinder is 100 pounds per square inch, it may readily be determined that the downward force applied to the piston is 100 pounds force. This force is applied through the shafts 30 and the pulling head 34 to the head 40 of the fastener, tending to extract the fastener from the roof surface 11.

It should be understood that the multiplier constant may also be determined by calibration. That is, if a known force of 100 pounds is directed upon the piston 52, and the pressure reading within the cylinder 50 is 25 pounds per square inch, the multiplier constant would be 4. The gauge 54 could then be specially calibrated with this multiplier.

The fluid pressure measurement gauge 54 includes two indicating needles; an actual pressure indicating needle 61 operated by the gauge mechanism in the conventional manner, and a maximum pressure indicating follower needle 62 driven by the needle 61. The actual pressure indicating needle 61 displays the actual pressure within the cylinder 50 at any given time. The maximum pressure indicating needle 62 displays the highest pressure within the cylinder 50 since the last time the maximum pressure indicating needle was reset by the reset knob 64.

Interaction of the various elements of the pullout force measuring apparatus 10 is now discussed. The closed end of the cylinder 50 of the compression force measuring assembly fits within the circular recess 29 between the slide bushings 28 in the base 12, and the cylinder is rigidly fixed to the base by welding, an adhesive, or other means known in the art, such that the conical depression 58 of the piston 52 is upwardly disposed.

The parallel shafts 30 slidably fit within the slide bearings 28 in the base 12, such that the upper end plate 32 is disposed above the compression force measuring assembly 16, and the pulling head 34 is disposed below the top platform 24 of the base 12. It should be understood that the parallel shafts 30 slide within the slide bearings 28, to allow the entire sliding parallel shaft assembly 14 to slide up and down relative to the base, such that the pulling head 34 may pass through the circular hole 26 in the floor portion of the base 12. Furthermore, a certain amount of lateral or angular "play" is provided between the shafts 30 and the slide bushings 28, to prevent binding of the shafts in the bushings during operation of the pullout force measuring device, as discussed in detail later in this application.

The threaded member 40 of the screw assembly 15 threadably accepts the fixed hex nut 36 in the upper end plate, and passes through the circular hole 35 in the upper end plate, such that the spike member 44 fits within the conical depression 58 in the piston 52.

Referring now to FIGS. 1 and 2, operation of the pullout force measuring apparatus 10 to determine the pullout force required to remove a typical headed fastener 39 from a roof 11 is now discussed. The pullout force measuring apparatus 10 is positioned upon a roof surface 11 such that the circular hole 26 in the floor plate 20 substantially encircles a typical fastener 39. The pulling head 34 is then positioned relative to the fastener 39 such that the head of the fastener fits within the T-shaped channel 37, as previously discussed.

The screw assembly 15 is rotated such that the spike 44 is biased on the top of the piston 52 in the conical depression 58, and the entire sliding parallel shaft assembly 14 is drawn upwardly relative to the base 12, including the pulling head 34. As the pulling head is drawn upwardly, the fastener typically resists removal, and therefore a tensile force is encountered in the parallel shafts 30. This tensile force is transmitted through the upper end plate 32 and threaded member 40 to an equal compressive force upon the piston 52 of the compression force measurement assembly 16. As previously discussed, such a downward force may be determined by observing the fluid pressure measuring gauge 54, and either directly reading the tensile force or multiplying the reading by the appropriate multiplier constant. Therefore it may be seen that the amount of upward tensile force applied to the fastener 39 is determined by observing the maximum pressure indicating needle 62 in the fluid pressure measuring gauge 54.

As the screw assembly is progressively tightened, the tensile force on the head of the fastener gradually increases until the fastener is removed from the roof 11. The maximum tensile force, or "pullout" force required to remove the fastener 39 may then be determined by observing the maximum pressure reading indicated by or corresponding to the maximum pressure indicating needle 62. As noted above, the apparatus 10 preferably is designed to produce a direct reading in pounds, kilograms, or the like, without requiring conversion charts or arithmetic manipulation of pressure readings.

As previously discussed, a certain amount of lateral play is provided between the shafts 30 and the slide bushings 28. This play reduces the chance of the shafts binding in the bearings, should the shafts become misaligned in the bushings. Furthermore, the mating connection between the spike 44 and the conical depression 58 of the piston 52 allows the threaded member 40 to pivot somewhat relative to the piston 52. Therefore it may be seen that the above-discussed mating configurations of the pullout force measuring apparatus 10 greatly reduces any error in the pullout force determinations due to binding of its various interacting elements.

Various elements of the pullout force measuring apparatus are readily available as off-the-counter items. The remaining elements may be readily fabricated in a conventional machine shop using routine manufacturing process. Therefore it made be seen that the pullout force measuring apparatus may be easily and cheaply made, and also readily serviced and repaired.

It will thus be seen that the present invention provides a novel and improved pullout force measuring device which is lightweight, inexpensive, and simple to operate and maintain.

While this invention has been described in specific detail with particular reference to the disclosed embodiments, it will be understood that many variations and modifications can be effected within the spirit and scope of the invention as described in the appended claims.

I claim:

1. A device for determining the amount of force required to remove a fastener anchored to a supporting member, comprising:
    a base for placement upon the supporting member, said base comprising a base support for placement on the supporting member, and a platform spaced outwardly from said base support;
    fastener gripping means operably associated with said base;
    force exerting means for exerting a tensile force on said fastener gripping means relative to said base, so as to withdraw the fastener from the supporting member, said force exerting means comprising;

a hydraulic cylinder mounted on said platform and containing a quantity of liquid;

a piston in said cylinder in operative association with said liquid; and force transfer means having a first location operatively associated with said gripping means for exerting tensile force thereon, and having a second location operatively associated with said piston for exerting a force on said piston proportional to said tensile force, said force transfer means comprising:

a threaded rod coaxially aligned with said piston, said threaded rod having a first end in axial force transfer relation to said piston and having means to rotate the threaded rod;

a threaded follower member engaging said threaded rod for axial movement relative thereto in response to rotation of the threaded rod; and a tension link operatively connected to said threaded member and extending inwardly from said platform to move said fastener gripping means outwardly from said base support in response to selected rotation of said threaded rod, thereby exerting said tensile force on the gripping means and fastener gripped thereby, and force measuring means operably associated with said force exerting means to measure the force required to withdraw the fastener from the supporting member, said force measuring means comprising a pressure gauge responsive to the hydraulic pressure of said liquid resulting from force of said piston, and operative to provide an indication having a predetermined relation to said tensile force exerted on the fastener.

2. A device as in claim 1, wherein:

said tension link comprises a pair of rods flanking said cylinder and extending inwardly from said platform toward said base support for operative engagement with said fastener gripping means; and each rod being loosely received in a bushing supported by said platform, thereby allowing said rods to move in and out relative to the platform notwithstanding axial nonparallelism between the rods and the longitudinal axis of said piston.

3. A device as in claim 1, wherein said first end of the threaded rod comprises an axially pivotable engagement with said piston, so as to minimize the effect of possible axial misalignment between the piston and the threaded rod.

4. An apparatus for determining the amount of upward force applied to a fastener anchored to a supporting member, comprising:

a base for placement atop said supporting member, said base defining a first surface;

a plate positioned above said first surface;

fastener gripping means positioned below said first surface;

a tension link intermediate said plate and said fastener gripping means, said tension link linking said plate and said fastener gripping means;

force exerting means intermediate said plate and said first surface of said base for applying a downward force to said first surface and also applying a substantially equal but opposing upward force to said plate, such that said plate exerts an upward force on said tension link which is transferred to said fastener gripping means such that said fastener gripping means exerts an upward force on said fastener; and means for measuring said force applied to said first surface of said base.

5. The apparatus claimed in claim 4, wherein said tension link is rigidly attached to said plate and said fastener gripping means.

6. The apparatus claimed in claim 4, further comprising a second tension link intermediate said plate and said fastener gripping means.

7. An apparatus for determining the amount of upward force applied to a fastener anchored to a supporting member, comprising:

a base for placement atop said supporting member;

load sensing means positioned on said base;

a plate positioned above said load sensing means;

fastener gripping means positioned below said load sensing means;

a tension link intermediate said plate and said fastener gripping means, said tension link linking said plate and said fastener gripping means;

force exerting means intermediate said plate and said load sensing means for applying a downward force to said load sensing means and also applying a substantially equal but opposing upward force to said plate, such that said plate exerts an upward force on said tension link which is transferred to said fastener gripping means such that said fastener gripping means exerts an upward force on said fastener; and means for measuring said load applied to said load sensing means.

8. The apparatus claimed in claim 7, wherein said tension link is rigidly attached to said plate and said fastener gripping means.

9. The apparatus claimed in claim 7, further comprising a second tension link intermediate said plate and said fastener gripping means.

10. The apparatus as claimed in claim 9, wherein said first and said second tension links are on opposing sides of said load sensing means.

11. An apparatus for determining the amount of upward force applied to a fastener anchored to a supporting member along a first axis, comprising:

a base for placement atop said supporting member;

a hydraulic cylinder positioned on said base, said cylinder having a closed end and an open end, containing a body of fluid, and having a longitudinal axis substantially parallel to said first axis;

a piston slidably positioned within said open end of said cylinder along a second axis substantially parallel to said first axis, such that said body of fluid is contained by said piston and said cylinder;

a sliding assembly, comprising:

a plate;

fastener gripping means;

a pair of elongate tension rods spaced a distance apart and each having a first end attached to said plate and a second end attached to said fastener gripping means, said sliding assembly slidably positioned relative to said base along an axis substantially parallel to said first axis, such that said plate is above said cylinder, said rods are on opposing sides of said cylinder, and said fastener gripping means is below said cylinder;

force exerting means intermediate said piston and said plate for applying a downward force to said piston and also applying a substantially equal but opposing upward force to said plate, such that said plate exerts an upward force on said rods which is transferred to said fastener gripping means such that said fastener gripping means exerts an upward force on said fastener;

means for measuring hydraulic pressure of said body of fluid, said pressure being proportional to the force applied to said fastener.

* * * * *